US006707469B1

(12) United States Patent
Kelly (10) Patent No.: US 6,707,469 B1
(45) Date of Patent: *Mar. 16, 2004

(54) SYNCHRONOUS EXECUTION IN A MEDICAL IMAGING SYSTEM (75) Inventor: Geoffrey Oliver Kelly, Brooklyn, NY (US)

(73) Assignee: General Electric Company, Schenectady, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 971 days.

(21) Appl. No.: 08/696,627

(22) Filed: Aug. 13, 1996

(51) Int. Cl.[7] .............................................. G06F 19/00
(52) U.S. Cl. ...................................... 345/744; 345/960
(58) Field of Search ................................ 345/326, 329, 345/334, 335, 356, 357, 969, 960, 700, 733, 762, 754, 705, 853, 854, 333; 395/793; 707/531

(56) References Cited

U.S. PATENT DOCUMENTS 5,297,249 A * 3/1994 Bernstein et al. ........... 345/356
5,452,416 A * 9/1995 Hilton et al. ............... 345/346
5,572,643 A * 11/1996 Judson ....................... 395/793
5,687,717 A * 11/1997 Halpern et al. .......... 128/903 X

* cited by examiner

Primary Examiner—Cao (Kevin) Nguyen
(74) Attorney, Agent, or Firm—Carl B. Horton, Esq.; Armstrong Teasdale LLP (57) ABSTRACT

A programmable, medical imaging system which incorporates algorithms for enhancing the usability of the system for clinicians is described. With respect to programmability, and in one aspect, the present invention relates to a programmable system which includes a learn mode usable for script generation. In the learn mode, a user can rehearse a sequence of actions and save those actions to be replayed later. In another aspect, the present invention is directed to an algorithm which provides a non-blocking, synchronous interface to an underlying asynchronous architecture. Generally, the algorithm decouples the client-server portion of the application from the synchronous development environment. Using this algorithm, a programmer can develop a non-blocking, highly interactive, client-server application without having to resort to asynchronous programming techniques. In yet another aspect, the present invention is directed to an overlap detection and correction algorithm which, in one form is integrated into a review template editor for creating review templates. The overlap detection and correction algorithm, in one embodiment, is a one or two boundary rectangular cell overlap detection and correction algorithm.

10 Claims, 9 Drawing Sheets

SYNCHRONOUS EXECUTION IN A MEDICAL IMAGING SYSTEM

FIELD OF THE INVENTION

This invention relates generally to medical imaging and more particularly, to a programmable imaging system.

BACKGROUND OF THE INVENTION

Medical imaging systems generally are utilized for imaging parts of patient's bodies for physician review. Different imaging technologies, sometimes referred to in the art as modalities, may be used for imaging patient body parts. Examples of imaging modalities include computed tomography (CT), magnetic resonance (MR), ultrasound, positron emission tomography (PET), and nuclear imaging.

With respect to generating, processing, and displaying medical images, the development of medical imaging applications generally requires significant software development effort. The development is usually performed by highly skilled software practitioners since specialized software skills are needed to develop graphical user interface (GUI) based medical imaging applications. The software engineers, however, have limited domain knowledge. The clinicians who actually use the software applications typically lack the software engineering skills required for developing the applications. It would be desirable to provide an imaging system which is highly usable so that clinicians can develop imaging applications.

Known "programmable" systems enable clinicians to generate customized imaging applications. The most simple type of customization, for example, allows customization of display screens for a particular physician or other requirements. More complex customizations are required, for example, for research institutions.

The known programmable imaging systems, however, have a number of shortcomings. For example, one known programmable system does not provide the capability of creating/customizing new GUI elements. In addition, such system is not integrated into the base system, which results in visual, functional, and usability problems. Also, only an experienced programmer can add functionality to the system.

The following sets forth additional shortcomings in known programmable imaging systems. These shortcomings generally relate to script generation and execution, asynchronous execution, and review template editor functions.

1. Script Generation and Execution

Scripts typically are utilized for controlling the display and processing sequence of medical image so that a physician who reviews the image can view the image data in a desired format. For example, a particular physician may prefer a particular sequence of views be displayed when viewing a particular organ. A script can be generated to control the image display so that the desired sequence of views is generated and displayed.

Generating fully functional and usable scripts from graphical user interface (GUI) based software applications is difficult. Typically, scripts are generated by recording GUI events, such as button clicks, and replaying the events in the same application. In many situations, however, it is desirable to produce output scripts that can be used within the context of a different processing environment. In these situations, the semantics of the actions performed by the user must be captured rather than a mere sequence of GUI events.

There are many examples of applications that provide facilities for recording and playing back GUI events at various levels. One such known program records the mouse movements, button presses and keyboard clicks, and replays these events. Even small changes to the GUI, however, requires that the events be re-recorded to capture the changes.

Another known application records the GUI widget (buttons, sliders, etc.) that was activated (pressed) rather than simple mouse and keyboard actions. This program alleviates the problem with minor GUI changes, but still requires playback of the created script on the original application. That is, this program only enables recording an application and playing it back using the same application. The scripts produced are not designed for use outside of the instrumented application. Additionally, the syntax of the output scripts produced are completely predetermined and are not user configurable.

2. Asynchronous Execution

Known medical imaging systems have a client server architecture. A major advantage of this architecture is that the application process can remain attentive to the user because the application does very little processing. Most processing is handled by servers. The servers, in turn, are "specialists" at providing a particular service and may in fact be running on specialized hardware, optimized for particular tasks. A good example of this specialization is a processing server having hardware acceleration of common image processing operations. The ability to access network distributed resources is a major advantage of the client-server architecture.

With respect to task execution in a client-server architecture, the application makes a request for some service. Because the servers(s) which process the requests can reside anywhere on the local area network, the application must wait for the operation to complete before reporting the results back to the user. The amount of time the application must wait depends on many factors, including the speed of the server. To remain interactive, the application must yield, which typically is performed by returning the execution thread to the idle state so that the application can respond to other user requests. This yielding function is fundamental to a highly interactive application. When the reply from the previously queued request arrives, the application must then restore the processing context of the application to its prerequest state and present the results of the operation. This process is commonly referred to as asynchronous behavior.

Experience has shown that implementation of the request-yield-reply paradigm introduces significant programming obfuscation because single operations must be broken up into multiple execution threads, state or context information must be managed to bind the request side to the reply side, and subtle, difficult to diagnose timing related errors can creep into the code due to multiple interactive asynchronous execution threads. The resulting code also is difficult to maintain. These factors have significantly reduced the productivity of programmers in this environment.

Moreover, the asynchronous execution application code is complex and advanced computer programming skills are required to develop code in this environment. For example, a six to eight week training period is typical for an experienced software engineer in the request-yield-reply development paradigm described above. Much of this training period is spent appreciating the finer points of asynchronous software programming. Further, the complexity of asynchronous programming makes it an unsuitable approach for most end users who are not usually software engineers. For the most part, developers of client-server applications have accepted the development inefficiencies of the request-yield-reply program paradigm as a penalty for the additional flexibility and high interactivity of client-server applications.

In addition, and in an attempt to avoid some shortcomings of asynchronous operation, some approaches exist in which database functions behave synchronously. For example, in one known approach, a programmer detects abnormally long operations and takes corrective actions. The mechanism used to implement this behavior is a polling mechanism where the GUI is frozen during the wait phase, i.e., it does not implement a true yield. In medical imaging and real time control applications where response latency must be very low, this type of mechanism may not be acceptable since an operator may have to respond to an emergency situation during long transactions. A further disadvantage of this approach is that long operations cannot be cancelled during the wait period. It would be desirable to provide a system in which application interactivity is preserved even during long transactions while eliminating the chores of coding in a request-yield-reply paradigm and maintaining its benefits.

3. Overlap Detection and Correction

In developing medical imaging applications, a frequent activity is to construct a review template. A review template is a graphical presentation of images, curves, text and other patient information relevant to the review of medical diagnostic information. In constructing a review template, rectangular cells typically are constructed, the arrangement of the cells on the screen is selected, and the specification of attributes for those cells is generated. Cells can contain images, curves, text, and other information relevant to the diagnostic process.

For many physicians who review patient information, the presentation and format of the information is very important. Therefore, many physicians demand personalized review templates to suit their personalized diagnostic needs. To enable end user customization of review templates, an imaging system must provide an easy method for constructing or modifying review templates. In addition, the review template editors preferably are optimized for particular tasks.

One known system for constructing a review template includes the use of graphical review template editors which provide a point and click interface for creating the templates. The graphical editor has been found to be an easy way for the end user to construct review templates.

One shortcoming of known review template editors, however, is that such systems require the user to correct for cell overlap. Specifically, the cells are tiled and never overlap because overlap would occlude important diagnostic information. The user therefore must painstakingly and meticulously position cells using the mouse or a property editor. To aid in this task, some review template editors include tools such as a zoom mode to enable more accurate alignment. Other known systems provide tiling post-processors which pack the cells in a minimal geometric configuration. For medical imaging review template construction, these tools are either too time consuming in execution or lack flexibility because they do too much for the user, as in the case of the tiling post-processors. It would be desirable to provide an automatic overlap detection and correction algorithm which enables increased ease of use by accelerating manual cell alignment tasks.

The above described shortcomings associated with known programmable systems preferably would be overcome in a programmable system which is extremely user friendly so that clinicians can relatively easily and quickly develop imaging applications. In addition, and with respect to scripts, such scripts preferably could be used in many different environments so that regardless of the environment, images and data can be displayed for physician review in accordance with that physician's desires without significant additional effort and expense. Generation of such scripts also preferably would be simplified and interactive. Further, and as described above, it would be desirable to provide a system in which application interactivity is preserved even during long transactions while eliminating the chores of coding in a request-yield-reply paradigm and maintaining its benefits. Also, and for review template generation, it would be desirable to provide an automatic overlap detection and correction algorithm which enables increased ease of use by accelerating manual cell alignment tasks.

SUMMARY OF THE INVENTION

These and other objects may be attained in a programmable, medical imaging system which incorporates algorithms for enhancing the usability of the system for clinicians. With respect to programmability, and in one aspect, the present invention relates to a programmable system which includes a learn mode usable for script generation. In the learn mode, a user can rehearse a sequence of actions and save those actions to be replayed later. The learn mode provides an intuitive starting point for the definition of a new user protocol because it allows the user to develop novel functionality with no programming effort.

More specifically, and with respect to the learn mode, the system includes an initialization/instrumentation subsystem which includes a configuration file, a table loader and an auto installer. In operation, the table loader reads in the configuration file and uses the information read from the configuration file to initialize a master table. Also, the auto installer uses the "Widget name" stored in master table to find the associated widget from the graphical user interface (GUI) application, and stores the widget id back in the master table.

A user, working at the system GUI, inputs a series of events which are recorded by the GUI event handler system. A code generator outputs a script command corresponding to each specified GUI action. Also, a code compression system extracts the output variables from the current command and the previous command, and compares the output variables to the ones and zeros in the compression code. If all the unmasked object name sub-expressions are the same, the output is considered to be a replacement of the previous output. The system tracks the previous output and deletes it if the new output is considered a replacement. The output from the code compression system generally is referred to as an output script.

The output scripts generated using the above described system are easily and readily transferable to other processing environments. In addition, such system is relatively easy to use as compared to known programmable systems, and is extremely user friendly. Moreover, the system interprets the sequence of user actions (e.g., key clicks and mouse movements) into output commands in a manner that captures the intent of the operations, rather than simply recording the actions themselves. For example, in order to add two images, the GUI may require the user to perform a series of actions such as selecting the images to add, selecting the add operation, applying the selected operation, and so on. With the present system, the output represents commands to add the images as the user intends rather than the process of selecting individual images.

In another aspect, the present invention is directed to an algorithm which provides a non-blocking, synchronous interface to an underlying asynchronous architecture. Generally, the algorithm decouples the client-server portion of the application from the synchronous development environment. Using this algorithm, a programmer can develop a non-blocking, highly interactive, client-server application without having to resort to asynchronous programming techniques.

The resulting code is synchronous, highly readable, compact and can be developed by a practitioner not familiar with programming in a client-server architecture. Further, this algorithm can be practiced on operating systems which have or do not have intrinsic support of multiple execution threads.

In yet another aspect, the present invention is directed to an overlap detection and correction algorithm which, in one form is integrated into a review template editor for creating review templates. The overlap detection and correction algorithm, in one embodiment, is a one or two boundary rectangular cell overlap detection and correction algorithm. The algorithm is non-packing so that it accurately carries out the intention of the user's alignment actions, and provides the important advantage of accelerating cell alignment tasks.

The above described programmable system is extremely user friendly and it is believed that clinicians can relatively easily and quickly develop imaging applications using the system. Also, scripts generated using the system can be easily transported for use in many different environments so that regardless of the environment, images and data can be displayed for physician review in accordance with that physician's desires without significant additional effort and expense. In addition, although a client-server architecture is utilized, system interactivity is preserved even during long transactions while eliminating the chores of coding in a request-yield-reply paradigm. Further, and with respect to review template generation, the automatic overlap detection and correction enables increased ease of use by accelerating manual cell alignment tasks.

BRIEF DESCRIPTION OF THE INVENTION

DETAILED DESCRIPTION OF THE DRAWINGS

The present invention, in one aspect, is directed to a programmable medical imaging system incorporating algorithms which enhance the system usability. The algorithms relate generally to learn mode script generation, synchronous operation, and overlap detection and correction in a review template editor. Importantly, the present invention can be practiced in many different medical imaging modalities and is not limited to practice in any one particular modality. A programmable system, in accordance with one embodiment of the present invention, is described below. In addition, the learn mode, synchronous operation, and overlap detection and correction routines are described below.

Programmable System Description

The programmable medical imaging system described herein can be implemented in many alternative hardware platforms including, for example, on a HP 715/100 UNIX based workstation commercially available from Hewlett-Packard Company, 250 North Patrick Boulevard, Suite 100, Brookfield, Wis. 53045. In one form, and by way of example, it is contemplated that the routines can be implemented in connection with, and integrated into, a nuclear imaging system such as the nuclear imaging system known as the GENIE™ system, which is commercially available from General Electric Company, GE Medical Systems, 3000 North Grandview Blvd., Waukesha, Wis. 53188. Of course, the routines can be implemented on many other platforms and in connection with many other medical imaging systems, including in systems other than nuclear imaging systems.

The following description relates to one embodiment of a programmable system which includes tools for script generation and other programmability related tasks. The tools can be implemented on the user workstation and are accessible to the user through a menu, as described below. To facilitate an understanding of the function of the tools, the steps of developing a new application, or script, are summarized below.

1. Populate the predefined protocol navigation area with the desired buttons.
2. Generate code by rehearsing the application's behavior on the GUI.
3. Customize the generated code if necessary.
4. Attach the generated code to the button(s).

The programmability tools preferably enable these four basic steps to be achieved with point-and-click actions. In addition, for simple applications, the tools preferably provide that no programming is required, and for more complex applications and additional flexibility, low level programming can be done using Visual Basic and C languages. A Visual Basic compiler for a Unix based system is commercially available from Summit Software Company, 4933 Jamesville Road, Jamesville, N.Y., 13078.

In one embodiment, and particularly in an implementation in the GENIE™ environment referred to above, a navigation user interface (UI) is modelled after existing GENIE™ protocols, and new navigation elements in the form of buttons and menus are added by simple point-and-click. A double-click on the button allows the user to attach behavior to that button. The behavior is usually to display a results screen or to perform a series of processing operations followed by the display of the results. Further, a live minified image area is always present and provides a "dashboard" for the application. The dashboard properties of the live image area provide instantaneous feedback on the effects of algorithmic modifications. This interactivity and transparency between development and execution of the application substantially eliminate the design-build-test cycle.

Figure 1A:
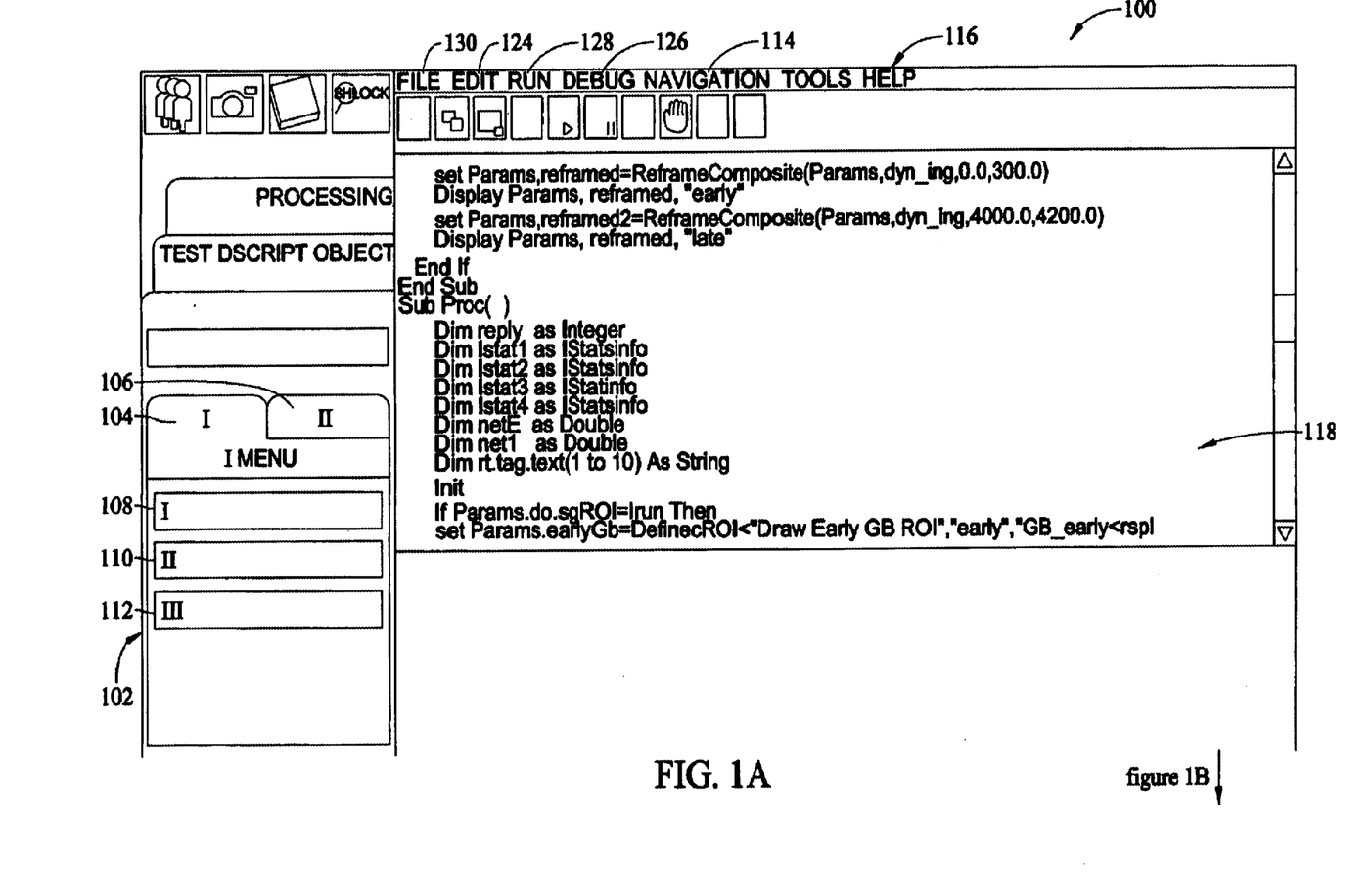
FIGS. 1A and 1B illustrate an exemplary user interface for a programmable system in accordance with one embodiment of the present invention.
Figure 1B:
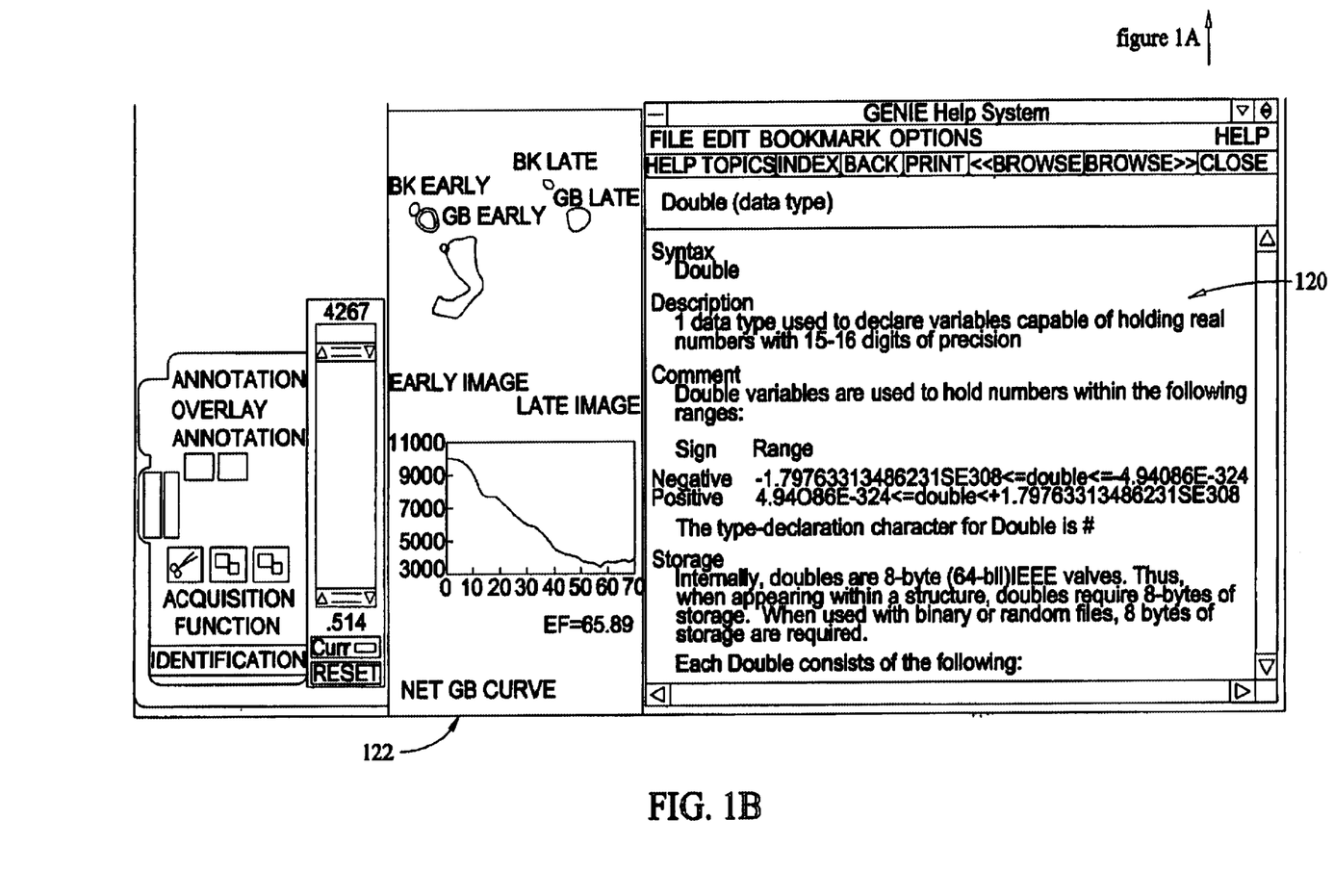

FIGS. 1A and 1B illustrate an exemplary user interface 100 configured for the GENIE™ system. As shown in FIGS. 1A and 1B, a navigation area 102 is being built. Two tabs 104 and 106 have been created, and first tab 104 contains three (3) buttons 108, 110 and 112. A "Navigation" menu item 114 for building navigation area 102 is provided on menu 116. Interface also includes a script editor window 118, and menu 116 illustrates various functions that may be selected by the user. An active help window 120 also is illustrated. Interface 100 further includes an image area 122 displaying medical images and data.

To facilitate specifying the behavior of an application, a point and click generator, an integrated editor, and an external interface are provided. The point and click code generator is provided to generate code which represents the semantics of the user actions, which allows the user to code by example. The integrated editor is provided so that complex code can be written for maximum flexibility, and the editor can also be used to customize the generated code. The interface to externally defined libraries is provided for performance critical computations and maximum flexibility. This external interface also provides quick availability to external functionality such as, for example, to an image processing functionality or to external data acquisition subsystems.

Many components also can be integrated into the programmability environment to provide a highly coherent tool for developing clinical applications. These components include a learn mode, a script editor, a script debugger, and a script executor. The learn mode enables a user to rehearse a sequence of actions and save those actions to be replayed later. Moreover, using the learn mode, a user may modify the sequence of actions. Learn mode provides an intuitive starting point for the definition of a new user protocol because it allows the user to develop novel functionality with no programming effort. The learn mode also is a good learning tool for a novice user because it provides a link between actions and the corresponding user protocol script. In one form, the learn mode provides the following.

1. A set of user actions can be recorded, saved and later used to build a protocol.
2. During recording, the generated text from the sequence of actions can be displayed.
3. Data loading and saving operations are recordable.
4. Review templates description are recordable.
5. Image and curve processing operations are recordable.
6. Image and curve statistics results are recordable.

Figure 2:
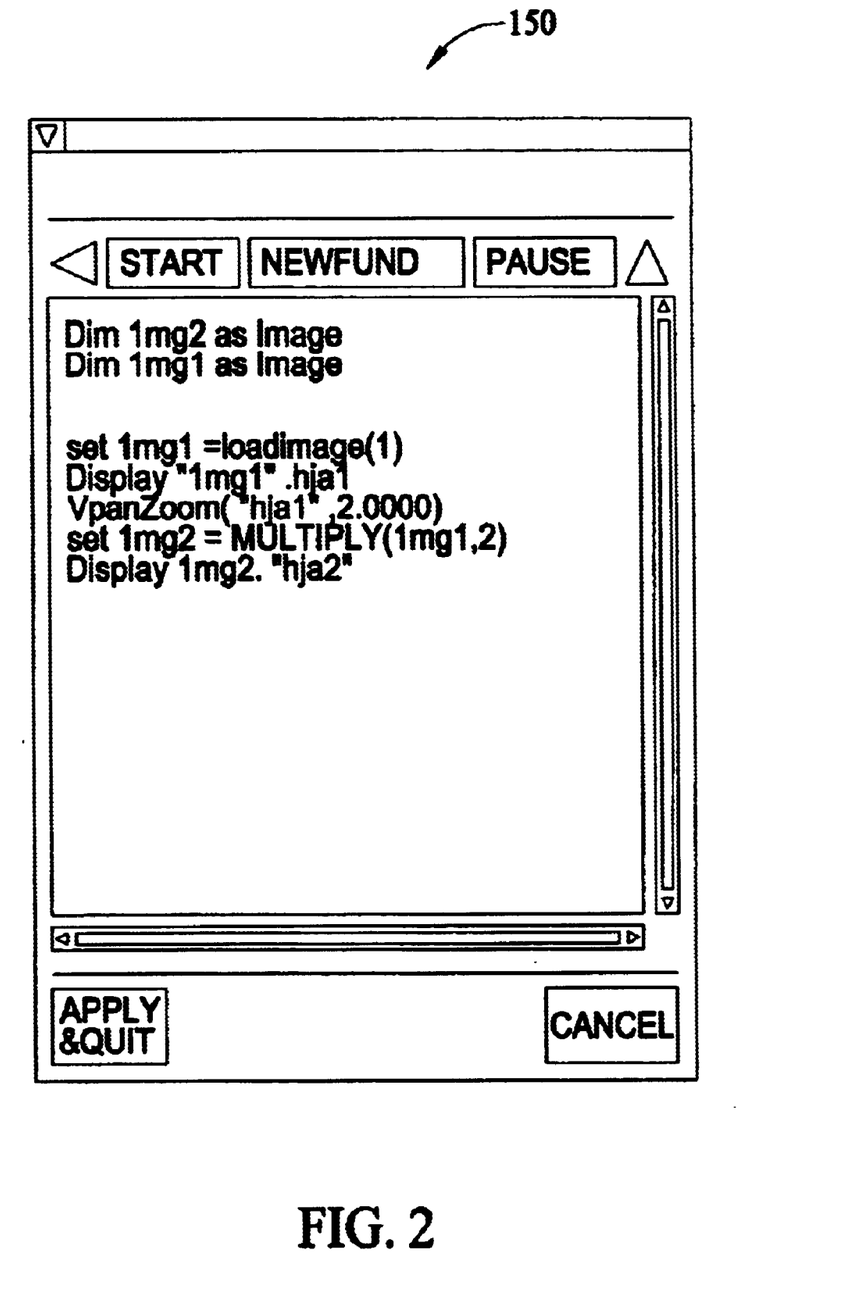
FIG. 2 illustrates an exemplary learn mode capture window displaying results of running learn mode.

An exemplary learn mode capture window 150 is shown in FIG. 2 where the results of running learn mode are shown. Further details regarding the learn mode are provided below in the next section.

Referring again to FIGS. 1A and 1B, a script editor 124 is provided to enable a user to edit user protocols. To facilitate easy entry and modification of the text for the user protocol, the following features can be provided. All of these features can be activated from a mouse or a keyboard.

1. Text editing facilities for Edit→Cut, Edit→Copy, and Edit→Paste.
2. Forward and backward text string searches. Searches can cover multiple text files.
3. Text string replacement.

A suitable script editor is commercially available from Summit Software Company, 4933 Jamesville Road, Jamesville, N.Y., 13078.

Still referring to FIGS. 1A and 1B, a script debugger 126 is provided to aid in the development and debugging of user protocols. Script debugger 126 executes the following functions.

1. A syntax check feature is provided. If an error exists the incorrect line is highlighted and the cursor is placed on the incorrect syntactical element. Additionally, a diagnostic message is displayed.
2. The user protocol can be executed one line at a time.
3. Functions/procedures can be stepped into, or can be executed as a single unit.
4. Breakpoints can be set at arbitrary lines in a user protocol. Execution of the user protocol will stop at the breakpoint. Breakpoints can be removed.
5. Variables can be inspected and modified during while in the debugger.

A suitable script debugger is commercially available from Summit Software Company, 4933 Jamesville Road, Jamesville, N.Y., 13078.

Running 128 a complete or partially complete user protocol is done by the script executor. Protocols can be tested incrementally by developing pieces of the protocol and then gradually filling out the functionality. The script executor provides this capability with the following features.

1. A protocol can be started from scratch. Execution will continue until completion or a interruption is encountered.
2. All image displays, dialogs, menus and tools are available to the user from the executor when the protocol is run. Essentially, the protocol runs just as it would if the user started the actual protocol. Note that scaled down image area 122 is displayed instead of the full screen image area.
3. A user protocol is suspendable at an arbitrary point by using a pause button. When resumed, execution continues from the point at which the user protocol was paused.
4. A user protocol can be interrupted at any time using a stop button.
5. All predefined and user defined function libraries must be available in the script executor.
6. Multiple protocols can run simultaneously and remain interactive. This is achieved by a time-slicing mechanism which ensures that all protocols receive some CPU time.

With respect to creating a new protocol, a user might modify an existing protocol and save the modified protocol as a new protocol. Alternately, a user may start from scratch. Conceivably, a user may even wish to delete existing protocols. These activities are generally referred to as protocol management. In one embodiment, the following features, all accessible from GUI 100, are available for managing protocols.

1. Manufacturer provided protocols can be copied, the copy can then be modified using a File→Save As feature (130).

2. Existing protocols can be viewed, i.e. the source script is always available to the user.
3. The user can create a new user protocol from scratch File→New (130).
4. An existing protocol can be modified File→Save (130).
5. An existing protocol can be deleted File→Delete (130).

In highly usable systems, there is a "look and feel" which all applications in that system obey. Similarly, and in the GENIE™ system, a look and feel is established for protocols. In one embodiment, navigation GUI builder 114 is provided to simplify the task of creating applications. Navigation GUI builder 114 provides the following.

1. Tabs, buttons, and menu items can be created using a point and click interface. No programming is required.
2. Property editors are provided for all navigation GUI builder elements. Properties include the specification of an "action" procedure and the visual properties of the element.
3. The completed navigation description is then saved with the protocol. When the protocol is executed the action property is invoked.

In one embodiment, a number of tools 132, including online hypertext help system 120, are provided. Help system 120 provides help on the usage of all elements of the programmability environment. In addition to this general help, comprehensive help on Visual Basic language is also provided. Help files are also provided for all new extensions to the language. A suitable hypertext help system is commercially available from Bristol Technology Inc., 241 Ethan Allen Highway, Ridgefield, Conn., 06877.

Scripts can easily be generated via help system screens. Specifically, a user can invoke a help screen and select a topic related to the script to be generated. A sample working code, or script, typically is included in the help file to aide the user in understanding a given function. The user can highlight the example and use the "copy" command to copy the example and use the "paste" command to paste the command to the script editor. The user can either use the script directly to execute a command or edit the script for inclusion in another script.

Figure 3:
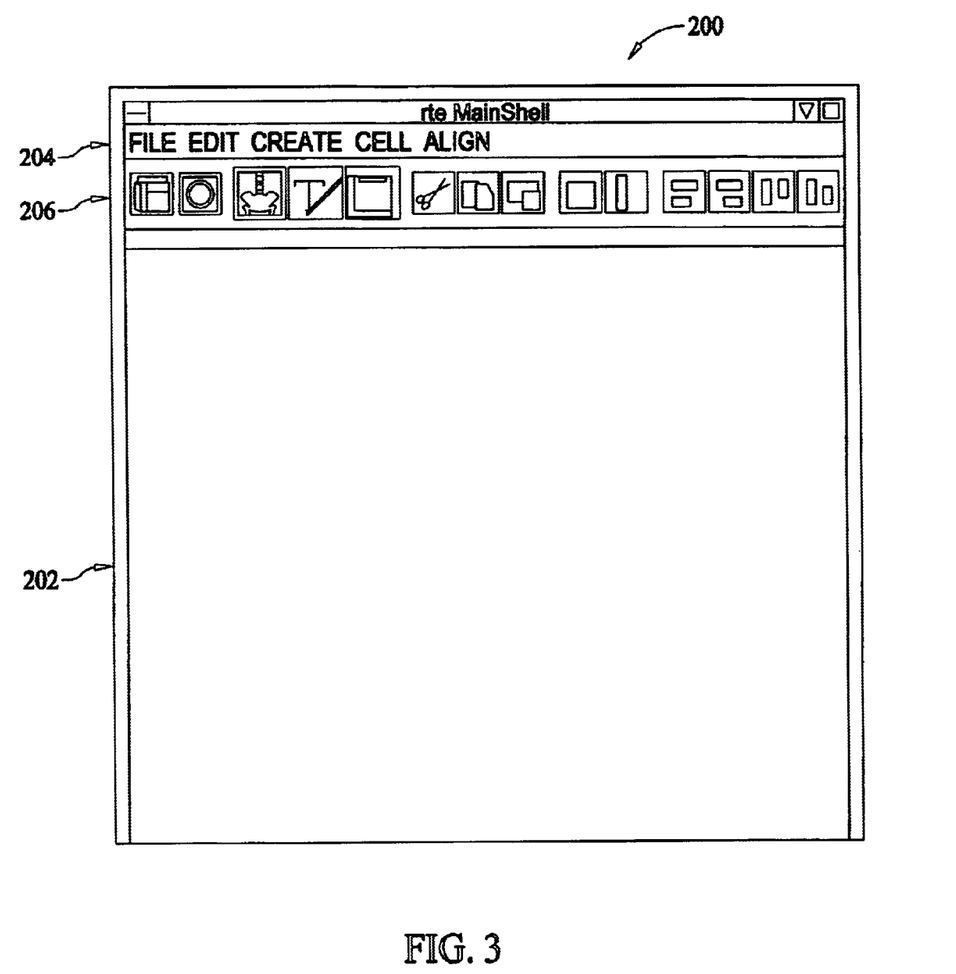
FIG. 3 illustrates an exemplary embodiment of a user interface for a review template editor.

With respect to a review template editor tool, and as described above, a review template is a screen layout, and the layout consists of cells where each cell can contain images (single or multiframe), curves, or overlay graphics. In one embodiment, a review template editor (RTE) enables a user to graphically construct a review template.

FIG. 3 illustrates an exemplary embodiment of a user interface 200 for an RTE. Interface 200 includes a display area 202 for displaying the cells created, and a "File" menu 204 is provided for enabling a user to easily select various functions. In addition, data processing commands 206 are provided to perform specific mathematical or clinical processing on image, curve and ROI data. A standard set of data processing commands and detailed help files for these data processing commands 206 are provided. The general functional areas addressed are image and curve arithmetic, image thresholding, image cut, copy and paste, image and curve statistics, image filtering (spatial and frequency), curve filtering, image reframing, image orientation (rotation, orientation and mirror), image sizing (arbitrary size), and ROI processing (logical operations).

Tools 132 enable a user to easily and quickly generate a program, i.e., a script. It is contemplated, of course, that not all tools 132 are necessary for each implementation and other tools may be desired in other implementations. The foregoing description of various tools, therefore, is by way of example only and not by way of limitation.

Learn Mode

Figure 4:
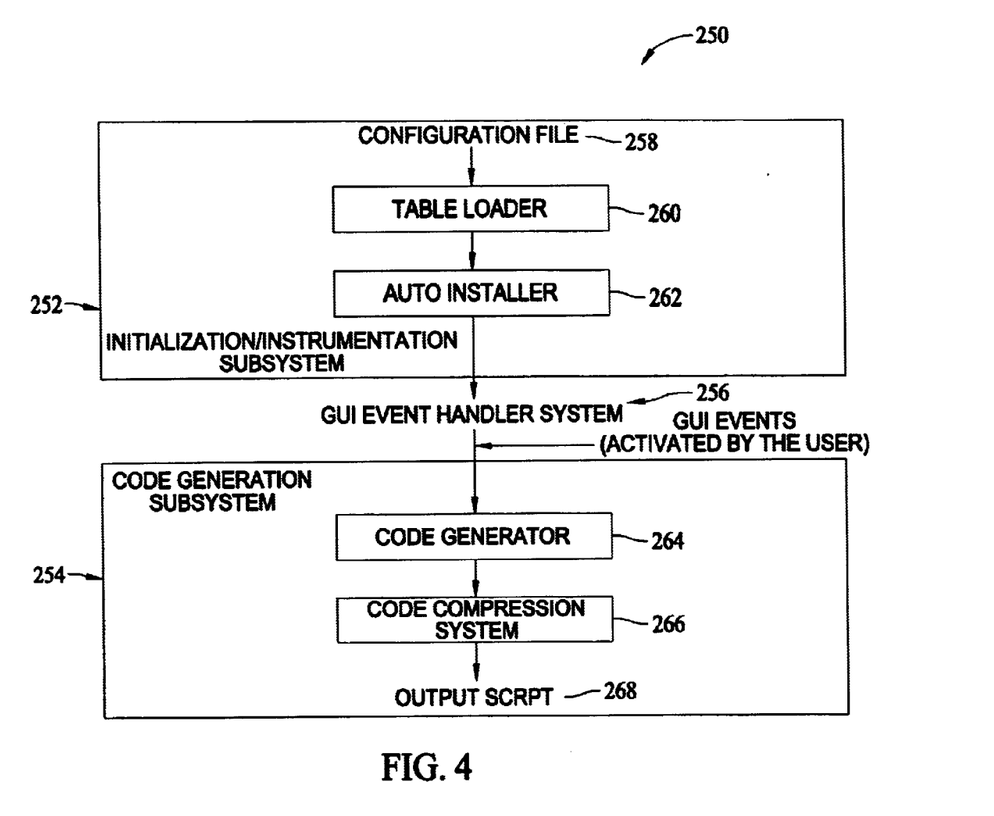
FIG. 4 is a block diagram illustrates a learn mode system in accordance with one embodiment of the present invention.

FIG. 4 is a block diagram illustration of an imaging system 250 including subsystems configured to achieve learn mode programmability in accordance with one embodiment of the present invention. As explained above, the learn mode enables a user to rehearse a sequence of actions and save those actions to be replayed later, and using the learn mode, a user may modify the sequence of actions. To implement learn mode in accordance with one embodiment of the present invention, imaging system 250 includes an initialization/instrumentation subsystem 252 and a code generation subsystem 254. A graphical user interface (GUI) event handler system 256 is provided for detecting events occurring at the GUI and providing such events to code generation subsystem 254. As described below in more detail, initialization/instrumentation subsystem 252 includes a configuration file 258, a table loader 260 and an auto installer 262. Code generation subsystem 254 includes a code generator 264 and a code compression system 266. An output script 268 is output by code compression system 266. Subsystems 252 and 258 are implemented, for example, in a user workstation.

Generally, and as an overview, configuration file 258 contains a list of all widgets in system 250 that need to be instrumented. The sequence (text string) that is used to generate output control script 268 is also represented in configuration file 258 alongside the corresponding widget name. Upon startup, configuration file 258 (which is stored in readable ASCII format) is loaded into an internal data structure. Starting from a base widget, the widget identifiers for each widget in the data structure are searched and recorded. During execution, when a certain widget (button, menu item, etc.) is activated (pressed), the output control script sequence is obtained from the internal data structure. This sequence is expanded, using specified rules, into a valid output control script 268. The control sequence, along with the specified rules, define a language for expressing output control script 268. System 250 is run-time configurable to output different syntax or commands by simply editing configuration file 258. In addition, the internal control sequence expansion logic can be easily extended to output different languages, including shell scripts. Moreover, system 250 interprets the sequence of user actions (e.g., key clicks and mouse movements) into output commands in a manner that captures the intent of the operations, rather than simply recording the actions themselves. For example, in order to add two images, the GUI may require the user to perform a series of actions such as selecting the images to add, selecting the add operation, applying the selected operation, and so on. With system 250, the output represents commands to add the images as the user intends rather than the process of selecting individual images.

Figure 5:
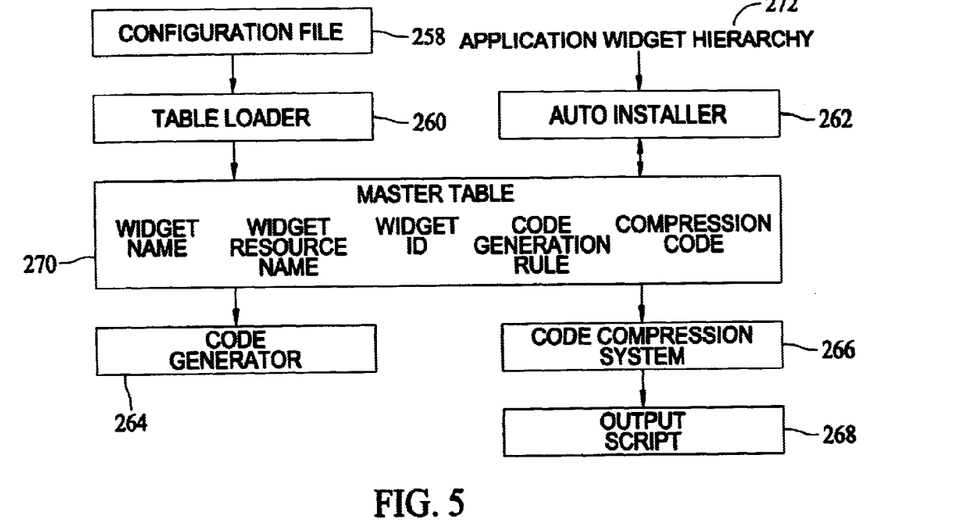
FIG. 5 is a data flow diagram illustrating data flow in the system illustrated in block diagram form in FIG. 4.

FIG. 5 is a data flow diagram illustrating, in more detail, operation of system 250. As described above, configuration file 258 contains different elements necessary for instrumenting a given application and generating output script 268. The following is a typical line in configuration file 258.

panUP: panZoomForm.panUp, NORMAL, O, C102G2, VpanY($0panScope, $0panY)

The above line contains six tokens (elements) which are described below.

1. Object Name ("panUP")
   This is the logical name of the command that is being instrumented, and is a case sensitive string of alphabetic characters (no numbers). The -name is referenced in the GenCode portion of the system which is described below.

2. Widget Name ("panZoomForm.panUp")
   This is the name of the widget being instrumented and should correspond to the unique path name for that widget. This string is used to look up the widget in the application widget hierarchy, and is NULL if the object does not correspond to a widget.
3. Object Type ("NORMAL")
   This specifies the type of the object. The possible choices are:
   MODAL
      This type of object does not generate a command directly and is used in situations where an object may have GenCode associated with it but no code is to be generated when the object is activated. Typically, any objects that alter the state of the applications are denoted as MODAL.
   DESTRUCTOR/CONSTRUCTOR
      CONSTRUCTOR and DESTRUCTOR widgets indicate, when activated, that the number of widgets may change and cause the auto installer 262 to reinstall all widgets.
   NORMAL is the generic type given to all widgets that are not any of the above types.
4. Group ("0")
   The group provides a convenient method for handling similar objects in a uniform manner.
5. Compression Code ("C102G2")
   This is an optional feature used to restructure output code. For instance, when a user drags a mouse across the screen, it may be desirable to produce a command at the end of the action rather than producing a command at each mouse position. The compression code describes a rule used to perform such compression.
6. GenCode ("VpanY($0panScope, $0panY")
   This specifies what rule is to be used in translating a GUI event to a valid output script.

The elements represented in configuration file 108 have a close relationship with the widget hierarchy of the application being instrumented and generated output script 268.

Table loader 260 reads in configuration file 258 at runtime and uses the information read from configuration file 258 to initialize an internal data structure 270 referred to herein as a master table. Having configuration file 108 as a run time loadable file speeds up development since the software does not have to be recompiled to make changes to the configuration, and also results in a smaller binary file since the file is not loaded unless needed.

Master table 270 is an internal data structure for storing all information read by table loader 260, as well as some information derived from the application GUI using auto installer 262 as described below. In addition to storing the information in configuration file, master table 270 also contains a field to store the widget identifier (id) of all the widgets that are instrumented. In one implementation, master table structure is as follows.

```
typedef struct {
   char            object[MAX_COM_LEN};
   char            button_name[MAX_WIDGET_NAME]
   Widget          w;
   LMCommandType   com_type;
   LMCompression   compression;
   char            GenCode;
}LMMasterTab;
```

Auto installer 262 uses the "Widget name" stored in master table 270 to find the associated widget from the GUI application, and stores the widget id back in master table 270. Auto installer 262 can be adapted to work with any GUI application that has a named widget hierarchy 272. In an XWindows application, for example, auto installer 262 finds the widget using the Xt command, i.e., XtNameToWidget.

To search for each widget, auto installer 262 requires the base widget id for the application, which is found by ascending application widget hierarchy 272 from a widget passed to system 250 as part of the initialization call until the widget of the appropriate name is found.

Figure 6:
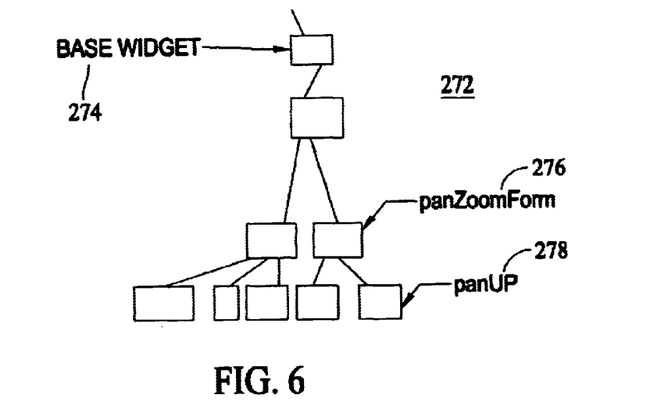
FIG. 6 illustrates an example of a widget hierarchy.

An example of widget hierarchy 272 is illustrated in FIG. 6. As shown in FIG. 6, exemplary widget hierarchy 272 includes a base widget 274. Located within this exemplary hierarchy is a panZoomForm type widget 276, which is generic to panZoomForm type instruments. A panUP widget 278 is a type of panZoomForm widget 276, and therefore, panUP 278 is located below, and connected to, panZoomForm type widget 276.

Referring again to FIG. 5, for all non MODAL objects, auto installer 262 attaches a callback to call a single callback function. Auto installer 262 also determines the type of widget. On being called by the "instrumented" widget, it is looked up in master table 270 and code generator 264 is called with the index into the entry.

Code generator 264 uses the GenCode portion of master table 270 to output a script command corresponding to specified GUI actions. Code generator 264 "evaluates" the text by expanding out any string that begins with $n(where n is a number) followed by alphabetic characters as regular expression: "$[0-9][a-zA-Z]+, e.g., $0panUp. The alphabetic characters represent the "object name". If the object to be evaluated is a widget, then the value of the widget is returned and replaces the "$n<object>" text in the output command. For example, if "panUp" was the object name for a text widget which contained the text "123.4", then in a GenCode string "print $0panUp" is changed to "print123.4" by looking in master table 270 for panUp.

Code generator 264 also expands out a $01F(" . . . "="  . . . ")<result> [$0else<else result>] expression. Both sides of the=are evaluated and then string compared. If true, the <result> is evaluated and used. If false, the <else result> is evaluated and used. The GenCode is simple to evaluate so that it does not need to use lex or yacc which would complicate and enlarge the code.

With respect to code compression system 266, sometimes referred to herein as a code compressor, code compression is controlled by the compression code read from configuration file 258. If the user repeats an action, e.g., zoom up, without code compressor 266, system 250 would generate a new command for each mouse button press. Code compressor 266 eliminates the duplicate lines as they appear. Code compression system 266 operates by extracting the output variables I(the $n<object name> expressions) from the current command and the previous command, and compares the output variables to the ones and zeros in the compression code. If all the unmasked object name sub-expressions are the same, the output is considered to be a replacement of the previous output. System 266 tracks the previous output and deletes it if the new output is considered a replacement.

In summary of the above described operation, table loader 260 reads in configuration file 258 and uses the information read from configuration file 258 to initialize master table 270. Also, auto installer 262 uses the "Widget name" stored in master table 270 to find the associated widget from the GUI application, and stores the widget id back in master table 270. A user, working at the system GUI, inputs a series of events, which are recorded by GUI event handler system 256. Code generator 264 outputs a script command corresponding to each specified GUI action. Code compression system 266 extracts the output variables from the current command and the previous command, and compares the output variables to the ones and zeros in the compression code. If all the unmasked object name sub-expressions are the same, the output is considered to be a replacement of the previous output. Compression system 266 tracks the previous output and deletes it if the new output is considered a replacement. Code compression system 266 outputs script 268.

Again, as explained above, system 250 provides the important advantages of being run-time configurable to output different syntax or commands by simply editing configuration file. Also, the internal control sequence expansion logic can be easily extended to output different languages, including shell scripts.

Synchronous Operation

In one aspect, the present invention is directed to an algorithm which provides a non-blocking, synchronous interface to an underlying asynchronous architecture. Generally, the algorithm decouples the client-server portion of the application from the synchronous development environment. The client portion, or unit, and the server portion, or unit, can reside on separate computers or on a single computer. Using this algorithm, a programmer can develop a non-blocking, highly interactive, client-server application without having to resort to asynchronous programming techniques. The resulting code is synchronous, highly readable, compact and can be developed by a practitioner not familiar with programming in a client-server architecture. Further, this algorithm can be practiced on operating systems which have or do not have intrinsic support of multiple execution threads.

Figure 7:
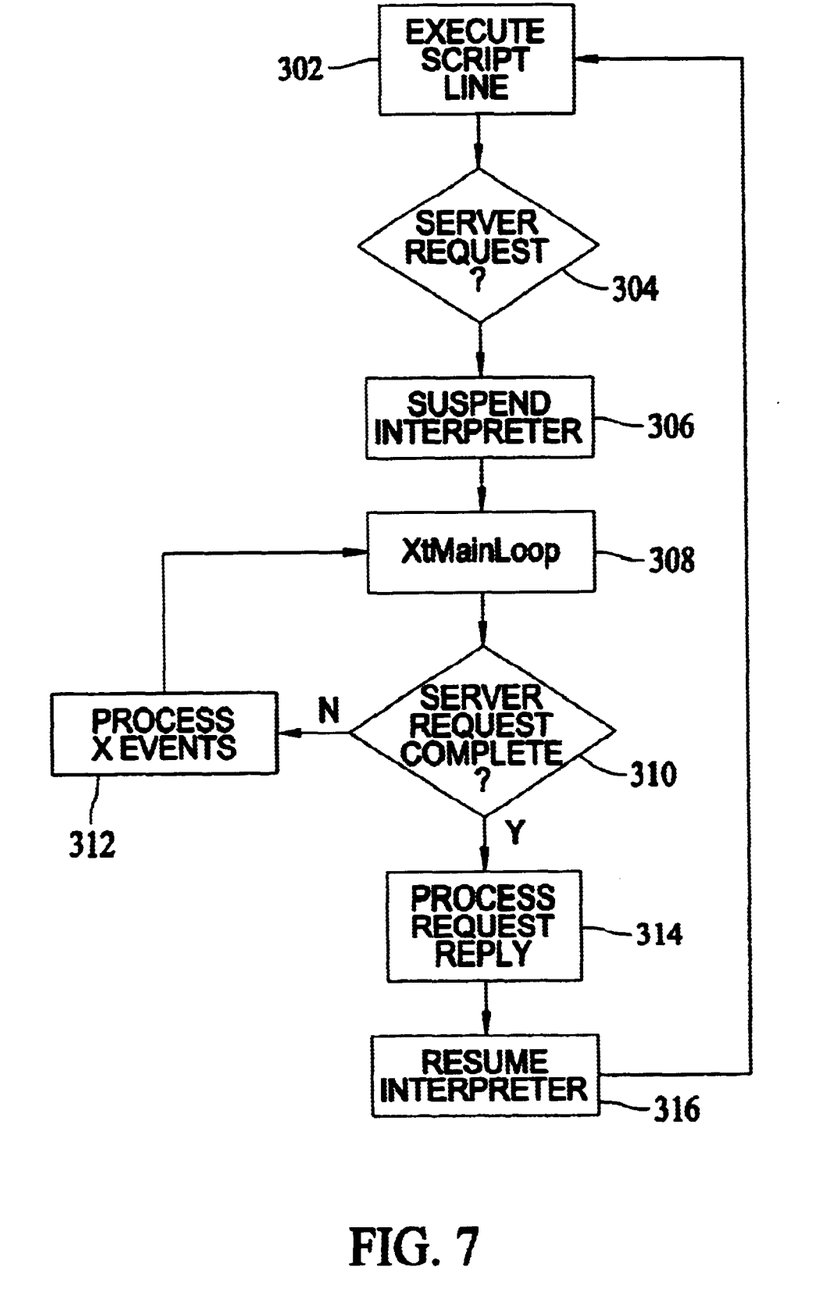
FIG. 7 is a flow chart illustrating a sequence of process steps for providing synchronous execution in accordance with one embodiment of the present invention.

Referring to FIG. 7, which is a flow chart 300 illustrating a sequence of process steps for providing synchronous execution in accordance with one embodiment of the present invention, the client-server portion of the application is the code which handles the request-yield-reply details. The development environment is an embedded interpreter. Both subsystems inhabit the same process with a single execution thread, however, the algorithm is practicable for multiple execution threads.

Referring specifically to FIG. 7, the end user develops code or scripts at run-time. In turn, the code is executed 302 by the interpreter. For those script commands which require a client-server transaction, i.e., a server request 304, the interpreter is programmed to invoke the appropriate functionality in the client-server portion of the application. Prior to and/or after making server request 304, the client-server portion of the application suspends the interpreter and yields 306. The client-server which manages the GUI remains interactive during the wait period. Time critical and real-time handling features, if kept in the client-server portion of the application, are live during the wait period because the client-server has yielded.

To remain interactive, the execution thread is returned to the idle state (XtMainLoop) 308. If the service request is not complete 310, events are continued to be processed 312. When the reply corresponding to the request arrives and is processed 314, the interpreter portion of the application is resumed 316, and the interpreter's program counter (PC) then continues from where it was suspended. Processing then returns to executing script lines 302.

Figure 8:
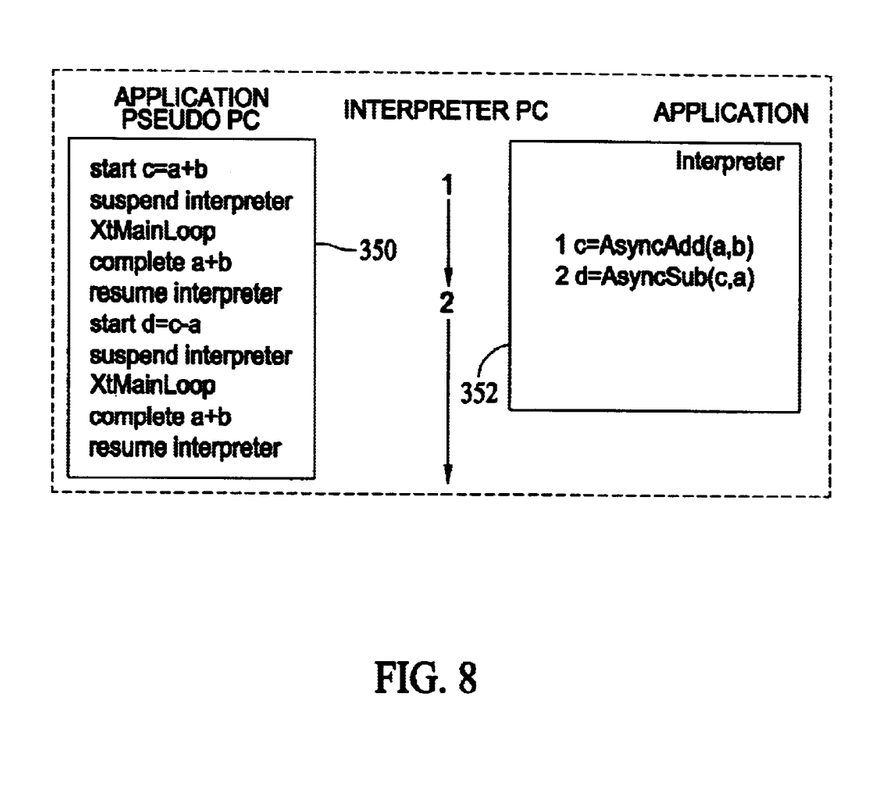
FIG. 8 illustrates an exemplary decoupled synchronous command execution in accordance with one embodiment of the present invention.

FIG. 8 illustrates an example of decoupled execution in accordance with the process steps shown in FIG. 7. In this example, two asynchronous operations must be performed. In box 350, high level tasks of the client-server side are shown. These tasks represent several lines of real code, so the program counter (PC) shown does not correspond directly to the actual processor PC. The middle column shows the progression of the interpreter PC as the client-server pseudo PC changes. Note that the client-server PC changes much more rapidly than the interpreter PC and that the interpreter PC stalls during an asynchronous operation. In box 352, application tasks are shown. The interpreter PC is bumped when the asynchronous operation completes.

In one specific implementation, a commercial Basic interpreter is embedded into the application. The interpreter is delivered as a library which is linked with the application. The interpreter library provides facilities for suspending the interpreter, resuming the interpreter, extending the programming language, calling functions in the client-server application, executing script functions/subroutines from the client-server application, and passing information between the interpreter and the application. The application runs under the UNIX operating system and uses the X Windowing system. Specifically, the application consists of the X Intrinsics (Xt), the Motif Widget toolkit (Xm) and the X protocol library Xlib. Additional client-side libraries are also used by the application to communicate with the respective servers. Extensions are added to the Basic language using the document extension mechanisms provided by the interpreter library. The extensions perform tasks by invoking client-server functions. The application is implemented without the use of explicit operating system support for threads, i.e., a single execution thread for the application process. The application, however, is suitable for operating systems which support multiple execution threads per process. Support for multiple execution threads would enhance the performance of this technique because less stack unravelling would be needed.

As described above, the code is synchronous, highly readable, compact and can be developed by a practitioner not familiar with programming in a client-server architecture. Further, the algorithm can be practiced on operating systems which have or do not have intrinsic support of multiple execution threads.

Overlap Detection and Correction

As described above, a review template is a graphical presentation of images, curves, text and other patient information relevant to the review of medically diagnostic information. In constructing a review template, rectangular cells typically are constructed, the arrangement of the cells on the screen is selected, and the specification of attributes for those cells is generated. Cells can contain images, curves, text, and other information relevant to the diagnostic process. The cells are tiled and preferably do not overlap because overlap would occlude important diagnostic information. In one aspect, the present invention is an automatic overlap detection and correction algorithm which enables increased ease of use by accelerating manual cell alignment tasks.

More specifically, and in one form, a one or two boundary rectangular cell overlap detection and correction algorithm is provided. The algorithm is non-packing so that it accurately carries out the intention of the user's alignment actions. The algorithm, in one form, is integrated into a review template editor for creating review templates (RTs).

Figure 9:
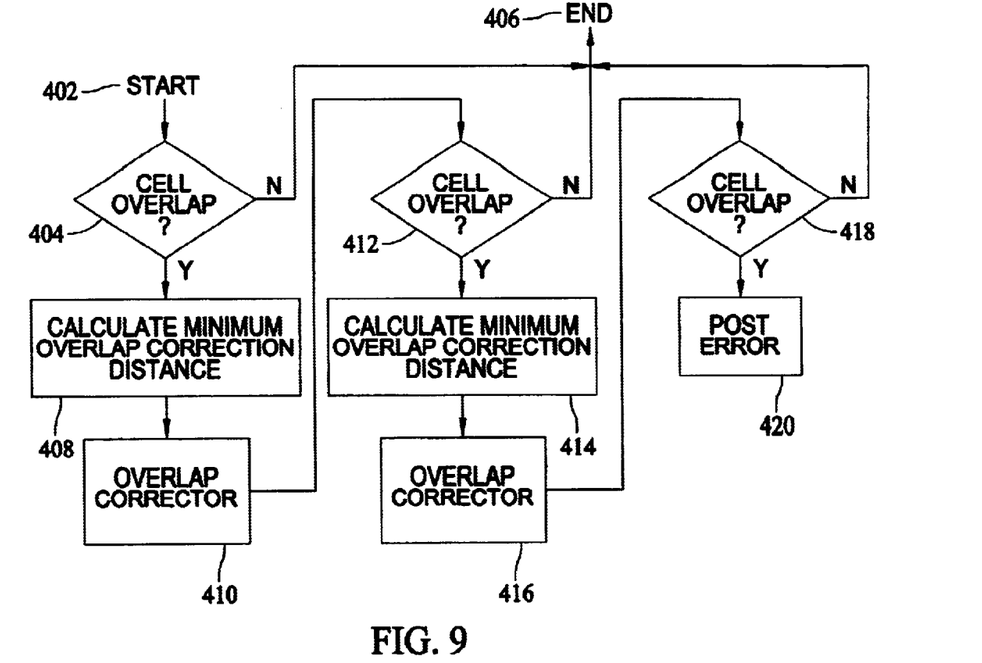
FIG. 9 illustrates a flow chart for one embodiment of a overlap detection and correction algorithm in accordance with one embodiment of the present invention.

A flow chart 400 for one embodiment of the overlap detection and correction algorithm is illustrated in FIG. 9. As shown in FIG. 9, the algorithm is a two pass interactive algorithm which attempts to eliminate overlaps when cell geometry is changed. Geometry changes can be to the cell dimensions or location.

More specifically, in response to a cell geometry change 402 (START), a cell overlap detector 404 is invoked. If no overlap is detected, the user request is carried out successfully 406 (END). If overlap is detected, an algorithm is called to compute the minimum distance $D_{min}$ that the changed cell must be moved to correct the overlap 408. $D_{min}$ is passed to an overlap corrector 410 which moves the cell by $D_{min}$. The $D_{min}$ shift can introduce further overlap in another area of the cell so overlap is checked for again 412. If the corrections caused no further overlap, the actions are carried out and the algorithm terminates successfully 406 (END). If further overlap is found, a new $D_{min}$ is calculated 414 and passed to overlap corrector 416 which moves the cell by the new $D_{min}$. The new $D_{min}$ shift also can introduce further overlap in another area of the cell so overlap is checked for again 418. If the corrections caused no further overlap, the actions are carried out and the algorithm terminates successfully 406 (END). If further overlap is found, then the overlap correction process is terminated with an error message to the user 420. No further correction passes are attempted because further passes could cause a packing of the cells. This packing action has undesirable side-effects, including that the cell may have to move relatively large distances for a potential fit, and further passes may never terminate (infinite search). The first side-effect, namely that the cell may end up in a location quite far from its original placement, violates a critical objective of maintaining the proximity of the cell to the user specified location.

Figure 10:
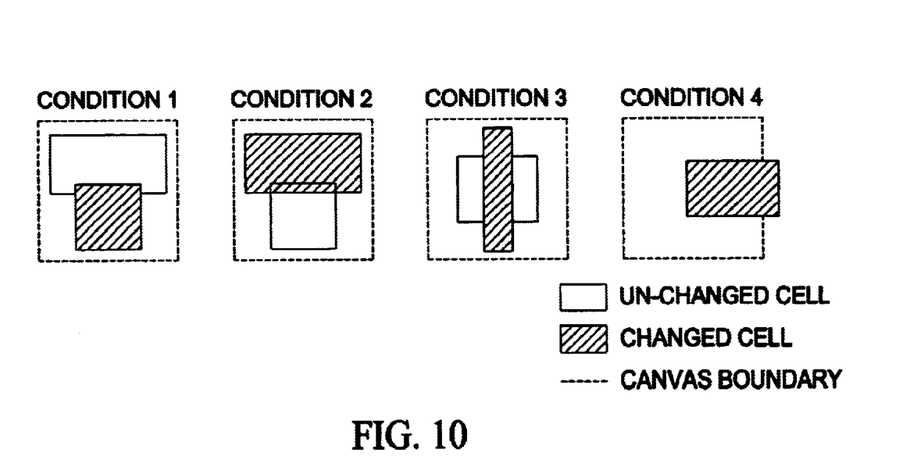
FIG. 10 illustrates cell overlap conditions checked in connection with a cell overlap detection and correction algorithm in accordance with one embodiment of the present invention.

Referring to FIG. 10, and with respect to determining cell overlap 404, 412 and 418, such overlap is determined by performing a linear check between the cell whose geometry has changed and the rest of the cells on the canvas. Four conditions are checked to determine cell overlap, and these conditions are illustrated in FIG. 10.

Condition 1. A corner of the changed cell is inside another cell.

Condition 2. A corner of another cell is inside the changed cell.

Condition 3. Two cells cross without any corners inside another cell.

Condition 4. The changed cell extends beyond the edge of the canvas.

The minimum distance $D_{min}$ the changed cell needs to be moved in order to correct overlap from one of the cells is found by determining the following distances for each cell the moved cell overlaps, and returning the minimum.

1. Distance from the top of the moved cell to the bottom of the overlapped cell.
2. Distance from the bottom of the moved cell to the top of the overlapped cell.
3. Distance from the left side of the moved cell to the right side of the overlapped cell.
4. Distance from the right side of the moved cell to the left side of the overlapped cell.

In the cases where two cells are minimally overlapped, the routine will save the leftmost minimally overlapped cell. If this is still not sufficient to uniquely identify one cell as minimally overlapped, the lowermost minimally overlapped cell is returned.

Overlap correction routine 410 and 416 takes the minimally overlapped cell and the minimum distance as input. The cell is then moved the minimum distance in the direction which corrects the overlap. In the case of the minimum distance being equal in two or more directions, the changed cell is moved in the following priority: right, left, up and down. These priorities are evaluated sequentially until a direction is found which will fix the overlap. The overlap detection and correction algorithm provides the advantage that tiling the cells is substantially automated and is user interactive to avoid piling.

The above described programmable system is extremely user friendly and it is believed that clinicians can relatively easily and quickly develop imaging applications using the system. Also, scripts generated using the system can be easily transported for use in many different environments so that regardless of the environment, images and data can be displayed for physician review in accordance with that physician's desires without significant additional effort and expense. In addition, although a client-server architecture is utilized, system interactivity is preserved even during long transactions while eliminating the chores of coding in a request-yield-reply paradigm. Further, and with respect to review template generation, the automatic overlap detection and correction enables increased ease of use by accelerating manual cell alignment tasks.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A method for executing commands in a client-server based medical imaging system, the medical imaging system including at least one client unit and at least one server unit, the client unit having a graphical user interface and an interpreter for executing a plurality of scripts, each script including script commands, said method comprising the steps of:

operating the interpreter to execute the scripts; and upon executing a script command requiring a server transaction, transmitting the server request from the client unit to the server unit;

suspending the script containing the server request until a reply is received to the server request; and maintaining the graphical user interface interactive while awaiting the reply.

2. A method in accordance with claim 1 further wherein upon receipt of a server reply to the request, said method further comprises the steps of:

processing the server reply to the request; and resuming operation of the script containing the server request.

3. A method in accordance with claim 1 wherein maintaining the graphical user interface interactive comprises the steps of processing graphical user interface events.

4. A computer for a programmable medical imaging system, said computer comprising an interpreter and a graphical user interface, said interpreter configured to:

execute scripts, each script comprising script commands; and suspend execution of a script containing a server request upon execution of the server request until a reply to the server request is received, wherein said computer maintains said graphical user interface interactive while said script containing the server request is suspended, and said interpreter resumes operation of said script containing the server request upon receipt of a reply to the server request.

5. A computer in accordance with claim 4 wherein to maintain said graphical user interface interactive while said script containing the server request is suspended, said computer is configured to process graphical user interface events while said script containing the server request is suspended.

6. A computer in accordance with claim 5 further configured to execute remaining said scripts while said script containing the server request is suspended.

7. A computer for a programmable medical imaging system, comprising:

a graphical user interface, means for executing script commands;

means for transmitting a server request to a server unit;

means for suspending said executing means upon executing a script command requiring that a server request be transmitted until a reply to the server request is received; and means for maintaining said graphical user interface interactive while said executing means is suspended.

8. A computer in accordance with claim 7 wherein said means for maintaining said graphical user interface interactive while said executing means is suspended comprises means for processing graphical user interface events while said executing means is suspended.

9. A method for executing commands in a client-server based system, the system including a client unit and at least one server unit, the client unit having an interpreter for executing scripts having script commands and a graphical user interface, said method comprising the steps of operating the interpreter to execute script commands, and upon executing a script command containing a server request, transmitting the server request from the client unit to the server unit, suspending the script command containing the server request until a reply is received to the server request, and maintaining the graphical user interface interactive while the script command containing the server request is suspended.

10. A method in accordance with claim 9 wherein maintaining the graphical user interface interactive while the script command containing the server request is suspended comprises the steps of processing graphical user interface events.

* * * * *